(12) United States Patent
Sasaki

(10) Patent No.: US 8,047,215 B1
(45) Date of Patent: Nov. 1, 2011

(54) LAPAROSCOPIC LENS CLEANER

(76) Inventor: Larry Sasaki, Shreveport, LA (US)

( * ) Notice: Subject to any disclaimer, the term of this patent is extended or adjusted under 35 U.S.C. 154(b) by 588 days.

(21) Appl. No.: 12/231,386

(22) Filed: Sep. 2, 2008

Related U.S. Application Data

(63) Continuation-in-part of application No. 11/810,081, filed on Jun. 4, 2007.

(60) Provisional application No. 60/811,073, filed on Jun. 6, 2006.

(51) Int. Cl.
*B08B 3/00* (2006.01)
*A61B 1/12* (2006.01)

(52) U.S. Cl. ............... 134/95.2; 134/94.1; 134/95.1; 134/95.3; 134/99.1; 134/102.1; 600/157; 600/158; 600/159

(58) Field of Classification Search ............... 134/94.1, 134/95.1, 95.2, 95.3, 99.1, 102.1; 600/157, 600/158, 159
See application file for complete search history.

(56) References Cited

U.S. PATENT DOCUMENTS

| | | | | |
|---|---|---|---|---|
| 5,339,800 A | | 8/1994 | Wiita et al. | 128/4 |
| 5,386,817 A | * | 2/1995 | Jones | 600/104 |
| 5,400,767 A | * | 3/1995 | Murdoch | 600/157 |
| 5,464,008 A | * | 11/1995 | Kim | 600/157 |
| 5,697,888 A | | 12/1997 | Kobayashi et al. | 600/159 |
| 5,830,126 A | | 11/1998 | Odanaka et al. | 600/156 |
| 6,126,592 A | | 10/2000 | Proch et al. | 600/114 |
| 2004/0220452 A1 | * | 11/2004 | Shalman | 600/157 |

FOREIGN PATENT DOCUMENTS

JP 07275185 A * 10/1995

* cited by examiner

*Primary Examiner* — Michael Barr
*Assistant Examiner* — Charles W Kling
(74) *Attorney, Agent, or Firm* — R. Keith Harrison

(57) ABSTRACT

A laparoscopic lens cleaner which is suitable for maintaining the lens of a laparoscope in a clean, dry condition during a laparoscopic surgical procedure is disclosed. An illustrative embodiment of the laparoscopic lens cleaner includes an elongated cleaner sheath having a sheath interior, a fluid conduit provided in the cleaner sheath, a fluid discharge nozzle provided in the sheath interior and communicating with the fluid conduit, a gas conduit provided in the cleaner sheath and a gas discharge nozzle provided in the sheath interior and communicating with the gas conduit.

5 Claims, 7 Drawing Sheets

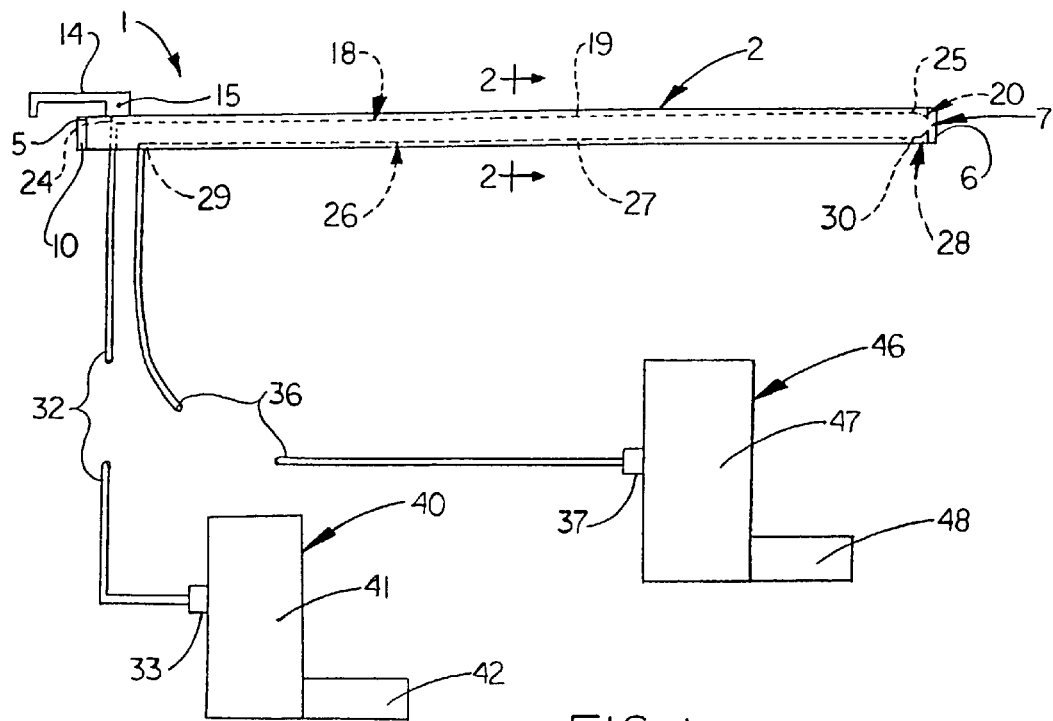
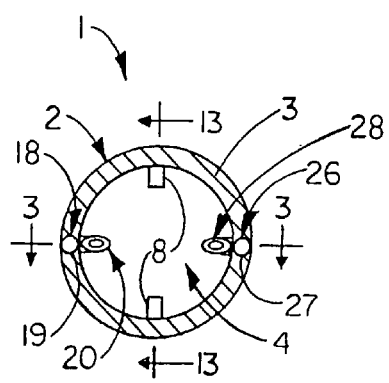
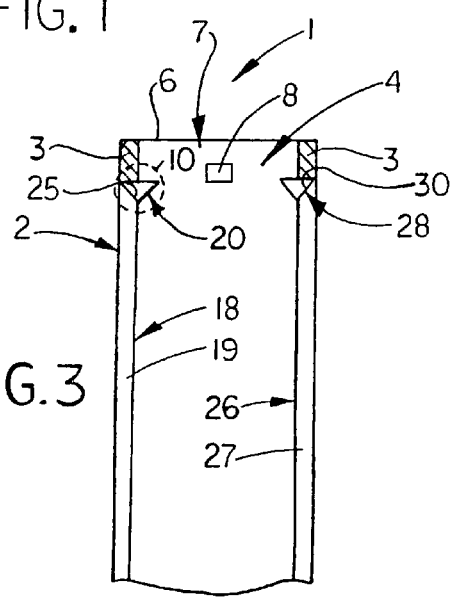
FIG. 1
FIG. 2
FIG. 3

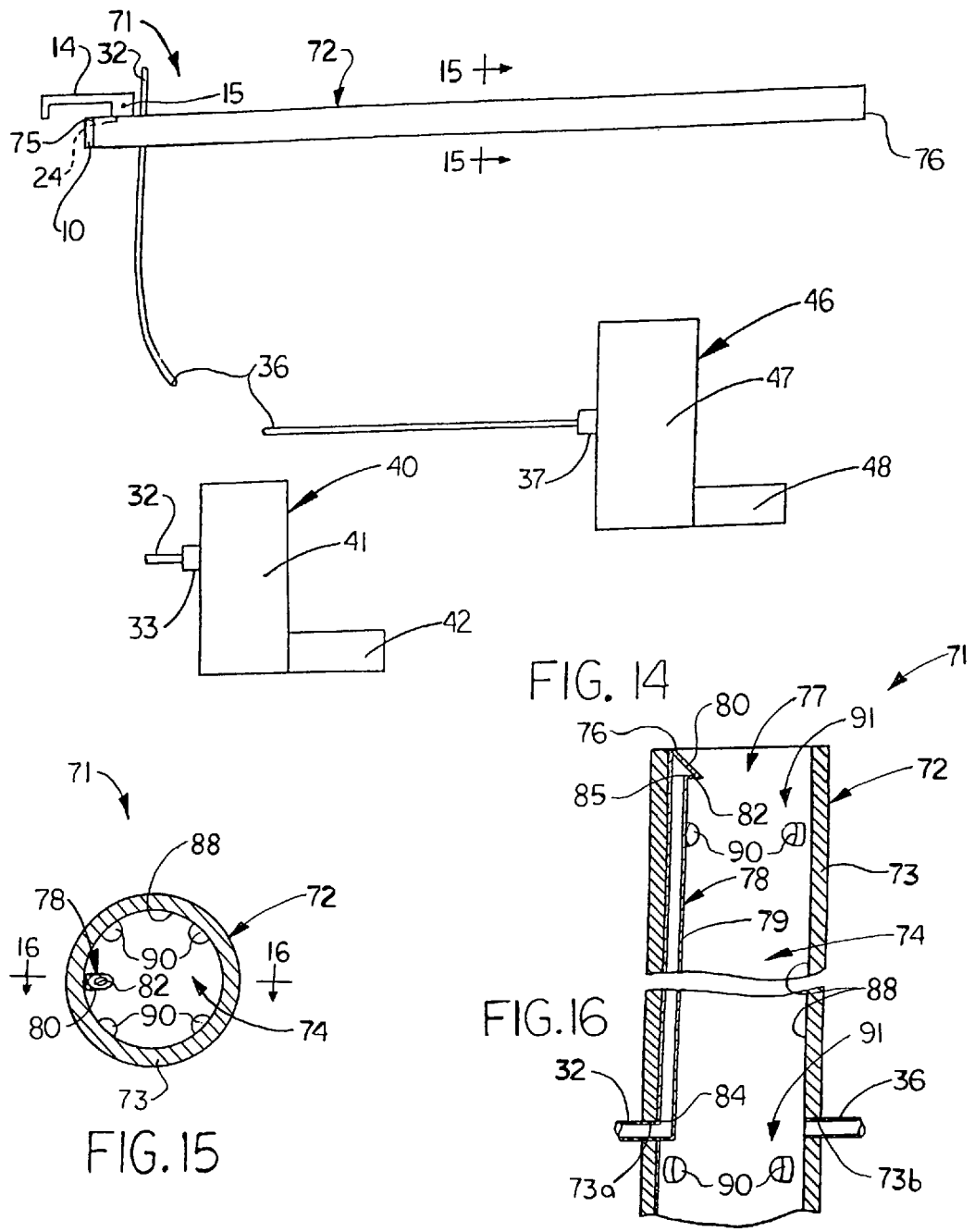

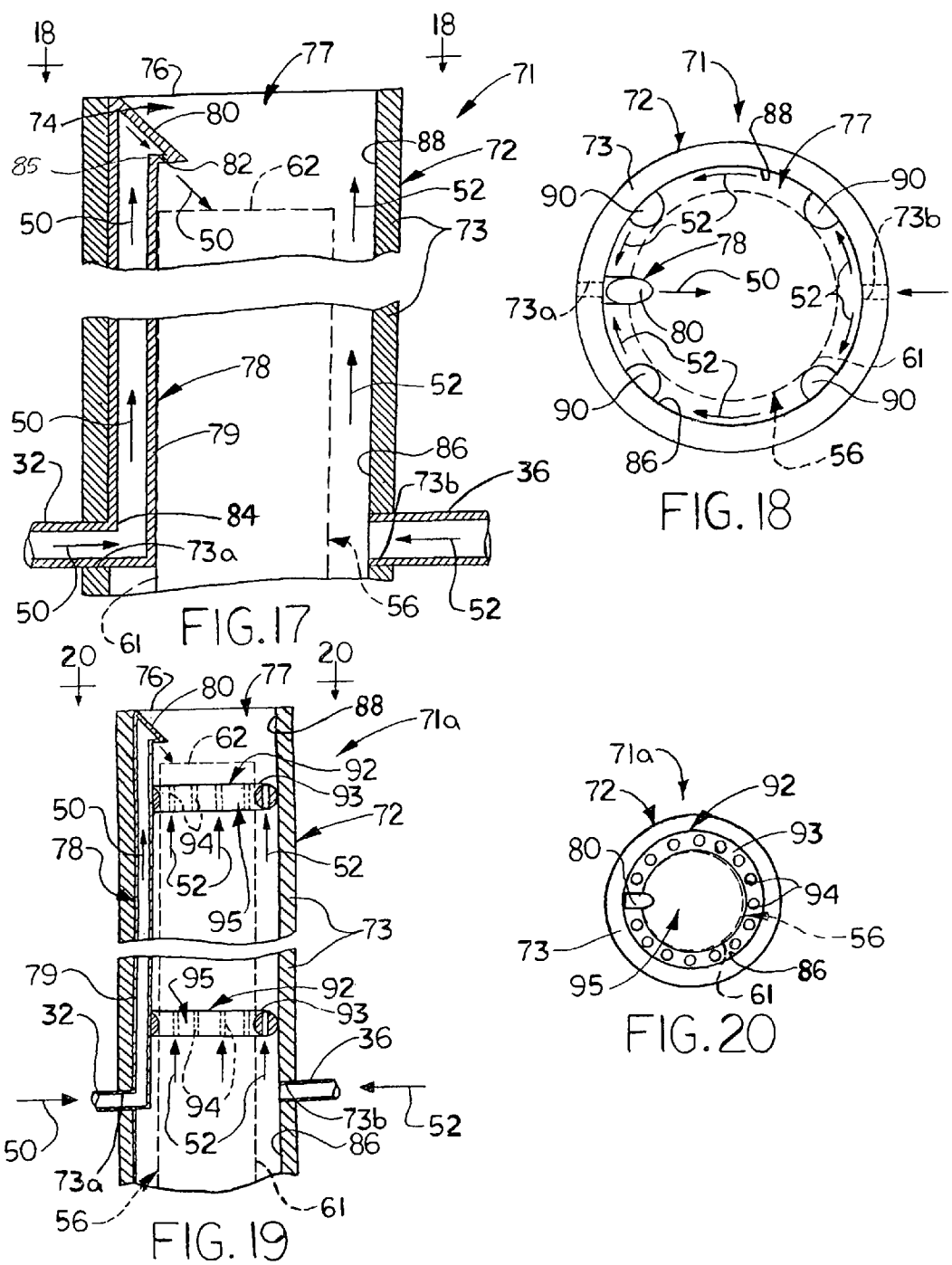

LAPAROSCOPIC LENS CLEANER

CROSS-REFERENCE TO RELATED APPLICATIONS

This is a continuation-in-part of prior filed copending U.S. patent application Ser. No. 11/810,081, filed Jun. 4, 2007 and entitled "Laparoscopic Lens Cleaner", which claims the benefit of and incorporates by reference in its entirety U.S. Provisional application No. 60/811,073, filed Jun. 6, 2006.

FIELD

The present disclosure relates to laparoscopes. More particularly, the present disclosure relates to a laparoscopic lens cleaner which is fitted over a laparoscope to maintain the lens of the laparoscope in a clean, dry condition during a laparoscopic surgical procedure.

BACKGROUND

Laparoscopes are surgical instruments through which anatomical structures in the abdomen and pelvis can be viewed by a surgeon. Laparoscopic surgery has become increasingly popular in recent years because it eliminates the need to cut a large surgical incision in a patient. This reduces patient recovery time and discomfort as well as the deleterious side effects associated with major surgery. In a laparoscopic surgical procedure, a small incision is initially cut in the abdominal wall of the patient to facilitate insertion of the laparoscope into the patient's abdomen or pelvis. Cannula sleeves can be inserted into the same incision or an adjacent incision or incisions to serve as entry ports for the extension of probes and other laparoscopic surgical instruments into the abdomen or pelvis. Laparoscopic surgery can be used to repair or remove internal tissues or organs as well as to aid in diagnostics since the contents of the abdomen or pelvis, including such anatomical structures as the fallopian tubes, ovaries, uterus, small and large intestines, appendix, liver and gallbladder, for example, can be viewed through the laparoscope.

A typical laparoscope includes a housing. An elongated lens shalt extends from one end of the housing, and a lens is provided in the distal end of the lens shaft. A camera viewfinder extends from the other end of the housing. A camera is connected to the housing and transmits images sighted through the lens to a television monitor on which the images are displayed. During a surgical procedure, the distal end portion of the lens shaft is extended into an incision in the patient's abdominal wall, while the proximal end portion of the lens shaft, the housing and the camera viewfinder remain outside the patient. One of the limitations of conventional laparoscopes is that the laparoscope lens frequently contacts and is obscured by blood, tissue and other matter during a laparoscopic surgical procedure. This adversely affects the quality of the images displayed on the television monitor.

SUMMARY

The present disclosure is generally directed to a laparoscopic lens cleaner which is suitable for maintaining the lens of a laparoscope in a clean, dry condition during a laparoscopic surgical procedure. An illustrative embodiment of the laparoscopic lens cleaner includes an elongated cleaner sheath having a sheath interior, a fluid conduit provided in the cleaner sheath, a fluid discharge nozzle provided in the sheath interior and communicating with the fluid conduit, a gas conduit provided in the cleaner sheath and a gas discharge nozzle provided in the sheath interior and communicating with the gas conduit.

BRIEF DESCRIPTION OF THE DRAWINGS

The disclosure will now be made, by way of example, with reference to the accompanying drawings, in which:

FIG. 1 is a side, partially schematic view of an illustrative embodiment of the laparoscopic lens cleaner according to the present disclosure, with a fluid pump and supply apparatus and a gas pump and supply apparatus connected to the laparoscopic lens cleaner through respective connecting conduits (partially in section);

FIG. 2 is a cross-sectional view, taken along section lines 2-2 in FIG. 1, of a cleaner sheath element of the laparoscopic lens cleaner;

FIG. 3 is a longitudinal sectional view, partially in section, taken along section lines 3-3 in FIG. 2, of the cleaner sheath element of the laparoscopic lens cleaner;

FIG. 14 is a partially schematic side view of an alternative illustrative embodiment of the laparoscopic lens cleaner according to the present disclosure;

FIG. 15 is a sectional view, taken along section lines 15-15 in FIG. 14, of the cleaner sheath element of the laparoscopic lens cleaner;

FIG. 16 is a longitudinal sectional view, partially in section, taken along section lines 16-16 in FIG. 15, of the cleaner sheath of the laparoscopic lens cleaner;

FIG. 17 is a longitudinal sectional view, partially in section, taken along section lines 16-16 in FIG. 15, of the cleaner sheath element of the laparoscopic lens cleaner, with a laparoscope (illustrated in phantom) inserted in the cleaner sheath and more particularly illustrating typical discharging of a cleaning fluid and a drying gas against a laparoscopic lens of the laparoscope in typical use of the laparoscopic lens cleaner;

FIG. 18 is an end view, taken along viewing lines 18-18 in FIG. 17, of the cleaner sheath of the laparoscopic lens cleaner and the laparoscope (in phantom) inserted in the cleaner sheath, more particularly illustrating linear flow of the cleaning fluid and annular flow of the cleaning gas in the cleaner sheath in typical use of the laparoscopic lens cleaner;

FIG. 19 is a longitudinal sectional view, partially in section, of a cleaner sheath element of an alternative illustrative embodiment of the laparoscopic lens cleaner, with a laparoscope (in phantom) inserted in the cleaner sheath;

FIG. 20 is an end view, taken along viewing lines 20-20 in FIG. 19, of the cleaner sheath;

DETAILED DESCRIPTION

Figure 4:
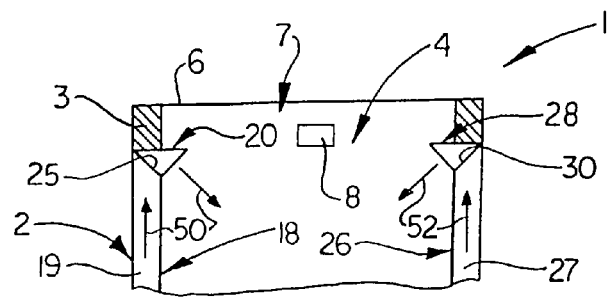
FIG. 4 is a longitudinal sectional view, partially in section, taken along section lines 3-3 in FIG. 2, of the cleaner sheath element of the laparoscopic lens cleaner, more particularly illustrating typical discharging of a cleaning fluid and a drying gas from respective discharge nozzles provided in the cleaner sheath element in typical use of the laparoscopic lens cleaner.

Referring initially to FIGS. 1-4 and 10-13 of the drawings, an illustrative embodiment of the laparoscopic lens cleaner according to the present disclosure is generally indicated by reference numeral 1. The laparoscopic lens cleaner 1 includes a generally elongated, cylindrical or tubular cleaner sheath 2 having a sheath wall 3 which may be a substantially rigid or semi-rigid plastic, for example. As illustrated in FIG. 2, the sheath wall 3 typically has a generally annular cross-sectional configuration and defines a sheath interior 4. As illustrated in FIG. 1, the cleaner sheath 2 has a proximal end 5 and a distal end 6 having a distal opening 7. As illustrated in FIGS. 2 and 3, at least one sheath flange 8, the purpose of which will be hereinafter described, may extend from the sheath wall 3 and into the sheath interior 4, generally at or adjacent to the distal end 6 of the cleaner sheath 2. As illustrated in FIG. 2, a pair of sheath flanges 8 may extend from the sheath wall 3 and into the sheath interior 4, typically in generally diametrically-opposed relationship to each other.

As illustrated in FIG. 1, an attachment clip 14 of selected design may be provided on the cleaner sheath 2, adjacent to the proximal end 5 of the cleaner sheath 2, to facilitate detachable attachment of the laparoscopic lens cleaner 1 to a laparoscope 56 (FIGS. 5 and 6) in typical use of the laparoscopic lens cleaner 1, as will be hereinafter described. The attachment clip 14 may be pivotally attached to the cleaner sheath 2 by a pivot pin 15. The typically spring-loaded attachment clip 14 is normally biased in the locking configuration which is indicated by the solid lines in FIG. 5 and may be pivoted against the spring-loaded bias to an unlocking configuration which is indicated by the phantom lines in FIG. 5. As illustrated in FIG. 1, a ring gasket 10 may be provided on the proximal end 5 of the cleaner sheath 2 to provide a seal between the cleaner sheath 2 and the laparoscope 56 when the laparoscopic lens cleaner 1 is provided on the laparoscope 56, as will be hereinafter described.

A fluid conduit 18 is provided in the cleaner sheath 2 and includes an elongated fluid distribution segment 19 which extends generally parallel to the longitudinal axis of the cleaner sheath 2. As illustrated in FIG. 1, the fluid distribution segment 19 has an inlet end 24 which is typically at or adjacent to the proximal end 5 of the cleaner sheath 2 and an outlet end 25 which terminates adjacent to the distal end 6 of the cleaner sheath 2. As illustrated in FIG. 2, the fluid distribution segment 19 of the fluid conduit 18 typically extends within and along the sheath wall 3 of the cleaner sheath 2. The diameter or width of the fluid distribution segment 19 may be substantially equal to or slightly larger than the thickness of the sheath wall 3.

Figure 10:
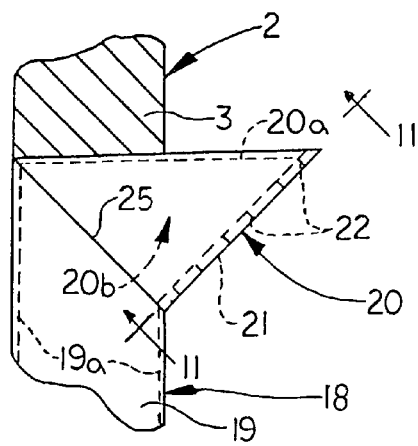
FIG. 10 is an enlarged sectional view, taken along section line 10 in FIG. 3, of a fluid discharge nozzle element of the laparoscopic lens cleaner.
Figure 11:
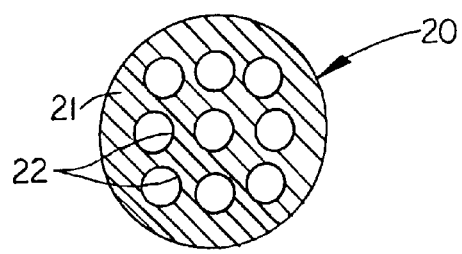
FIG. 11 is a cross-sectional view, taken along section lines 11-11 in FIG. 10, of a fluid discharge nozzle element of the laparoscopic lens cleaner, more particularly illustrating a multi-nozzle opening embodiment of the laparoscopic lens cleaner.
Figure 12:
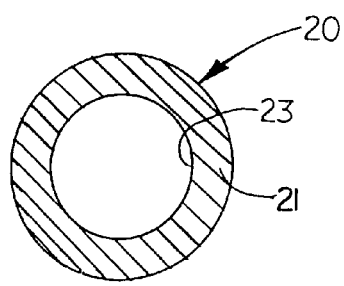
FIG. 12 is a cross-sectional view, taken along section lines 11-11 in FIG. 10, of a fluid discharge nozzle element of the laparoscopic lens cleaner, more particularly illustrating a single-nozzle opening embodiment of the laparoscopic lens cleaner.

As illustrated in FIG. 3, a fluid discharge nozzle 20 communicates with the outlet end 25 of the fluid distribution segment 19 and protrudes into the sheath interior 4, typically adjacent to the distal end 6 of the cleaner sheath 2. As illustrated in FIG. 10, the fluid discharge nozzle 20 has a nozzle wall 20a which is continuous with a segment wall 19a of the fluid distribution segment 19 and defines a nozzle interior 20b. The nozzle interior 20b of the fluid discharge nozzle 20 communicates with the fluid distribution segment 19. A nozzle plate 21 is provided in the nozzle interior 20b. As illustrated in FIG. 11, in some embodiments of the laparoscopic lens cleaner 1, multiple nozzle openings 22 extend through the nozzle plate 21 in a selected pattern to form a spray configuration of a cleaning fluid 50 (FIG. 4) as the cleaning fluid 50 is ejected through the nozzle openings 22, in use of the laparoscopic lens cleaner 1 as will be hereinafter described. As illustrated in FIG. 12, in other embodiments of the laparoscopic lens cleaner 1, a single nozzle opening 23 extends typically through the central portion of the nozzle plate 21 to form a single stream configuration of the cleaning fluid 50 as the cleaning fluid 50 is ejected through the nozzle opening 23. As illustrated in FIG. 1, a typically elongated, flexible fluid connecting conduit 32, which may be fitted with a conduit connector 33, is disposed in fluid communication with the inlet end 24 of the fluid distribution segment 19 and extends from the cleaner sheath 2 for purposes which will be hereinafter described.

A gas conduit 26 is further provided in the cleaner sheath 2 and includes an elongated gas distribution segment 27 which extends generally parallel to the longitudinal axis of the cleaner sheath 2. As illustrated in FIG. 1, the gas distribution segment 27 has an inlet end 29 which is typically at or adjacent to the proximal end 5 and an outlet end 30 which terminates typically adjacent to the distal end 6 of the cleaner sheath 2. As illustrated in FIG. 2, like the fluid distribution segment 19 of the fluid conduit 18, the gas distribution segment 27 of the gas conduit 26 typically extends within and along the sheath wall 3 of the cleaner sheath 2. The diameter or width of the gas distribution segment 27 may be substantially equal to or slightly larger than the thickness of the sheath wall 3. As further illustrated in FIG. 2, the gas distribution segment 27 of the gas conduit 26 may be positioned in generally diametrically-opposed relationship to the fluid distribution segment 19 of the fluid conduit 18, on the opposite side of the sheath interior 4. As illustrated in FIGS. 2 and 3, a gas discharge nozzle 28, which may have the same design as the fluid discharge nozzle 20, communicates with the outlet end 30 of the gas distribution segment 27 and protrudes into the sheath interior 4. As illustrated in FIG. 1, a typically elongated, flexible gas connecting conduit 36, which may be fitted with a conduit connector 37, is disposed in fluid communication with the inlet end 29 of the gas distribution segment 27 and extends from the cleaner sheath 2 for purposes which will be hereinafter described.

As further illustrated in FIG. 1, the fluid connecting conduit 32 is adapted for connection to a discharge outlet (not illustrated) of a fluid pump and supply apparatus 40, according to the knowledge of those skilled in the art, such as through the conduit connector 33 provided on the fluid connecting conduit 32, for example. The fluid pump and supply apparatus 40 may be conventional and includes a fluid reservoir 41 which is adapted to contain a cleaning fluid 50 (FIG. 4) such as saline solution, for example. The fluid pump and supply apparatus 40 typically further includes a foot pedal 42 which can be depressed to discharge the cleaning fluid 50 under pressure from the fluid reservoir 41 and into the fluid connecting conduit 32. Accordingly, responsive to depression of the foot pedal 42, the cleaning fluid 50 is discharged under pressure from the fluid pump and supply apparatus 40 and flows through the fluid connecting conduit 32 and the fluid distribution segment 19 of the fluid conduit 18, respectively. The cleaning fluid 50 is then discharged from the fluid discharge nozzle 20 into the sheath interior 4 of the cleaning sheath 2, as illustrated in FIG. 4, for purposes which will be hereinafter described.

The gas connecting conduit 36 is adapted for connection to an outlet of a gas pump and supply apparatus 46, according to the knowledge of those skilled in the art, such as through the conduit connector 37 provided on the gas connecting conduit 36, for example. The gas pump and supply apparatus 46, like the fluid pump and supply apparatus 40, may be conventional and includes a gas reservoir 47 which is adapted to contain a drying gas 52 (FIG. 4) such as carbon dioxide, for example. The gas pump and supply apparatus 46 typically further includes a foot pedal 48 which can be depressed to discharge the drying gas 52 under pressure from the gas reservoir 47 and into the gas connecting conduit 36. Accordingly, responsive to depression of the foot pedal 48, the drying gas 52 is discharged under pressure from the gas pump and supply apparatus 46 and flows through the gas connecting conduit 36 and the gas distribution segment 27 of the gas conduit 26, respectively. The drying gas 52 is then discharged from the gas discharge nozzle 28 into the sheath interior 4 of the cleaning sheath 2, as illustrated in FIG. 4, for purposes which will be hereinafter described. It is to be understood that the fluid pump and supply apparatus 40 and/or the gas pump and supply apparatus 46, instead of being foot-operated, may alternatively be any type of trigger-operated, button-operated or programmable apparatus known by those skilled in the art which is capable of containing and dispensing a cleaning fluid 50 and/or a drying gas 52, respectively, under pressure in a manually-controlled or automatic fashion.

Figure 5:
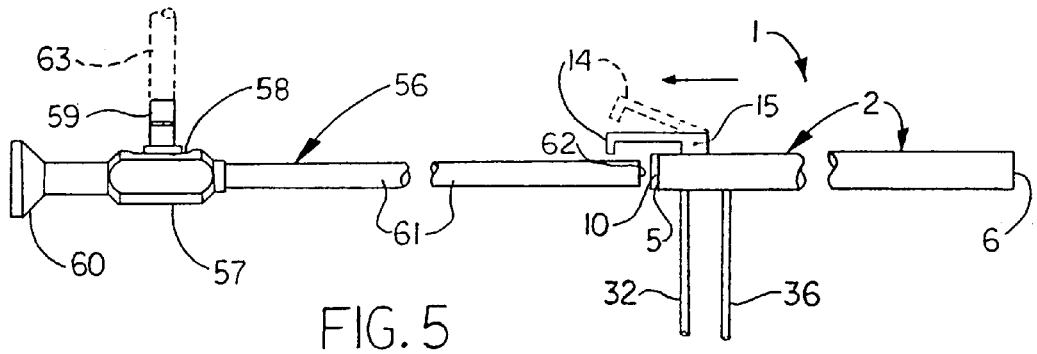
FIG. 5 is a side view, partially in section, of a laparoscope, preparatory to placement of an illustrative embodiment of the laparoscopic lens cleaner, partially in section, on the laparoscope in typical application of the laparoscopic lens cleaner.
Figure 6:
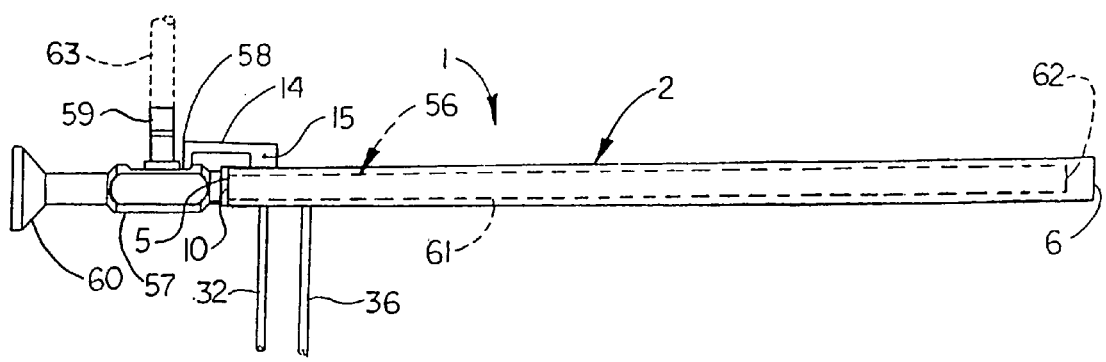
FIG. 6 is a side view, partially in section, of a laparoscope, with an illustrative embodiment of the laparoscopic lens cleaner fitted on the laparoscope in typical application of the laparoscopic lens cleaner.

Referring again to FIG. 1 and to FIGS. 5-9 and 13 of the drawings, in typical use, the laparoscopic lens cleaner 1 is provided on a laparoscope 56 (FIGS. 5 and 6) to periodically clean and dry a laparoscope lens 62 of the laparoscope 56 during a laparoscopic surgical procedure. As illustrated in FIGS. 5 and 6, the laparoscope 56 may be conventional and typically includes a laparoscope housing 57. A camera viewfinder 60 extends typically from one end of the laparoscope housing 57. An elongated lens shaft 61 extends typically from the end of the laparoscope housing 57 which is opposite the camera viewfinder 60. The laparoscope lens 62 is provided in the extending or distal end of the lens shaft 61. A camera attachment nipple 59 may extend from the laparoscope housing 57, typically between the camera viewfinder 60 and the lens shaft 61. The camera attachment nipple 59 is adapted for connection to a camera cord 63 which is, in turn, connected to a laparoscope camera (not illustrated). In typical use of the laparoscope 56, the viewfinder 60 is adapted to sight images of a surgical field typically in the abdominal or pelvic region of a patient 66 (FIG. 7) as the position of the laparoscope 56 is initially adjusted to view a particular anatomical structure or structures in the surgical field. The laparoscope camera, typically connected to the camera attachment nipple 59 through the camera cord 63, is adapted to receive images of the surgical field sighted through the laparoscope lens 62 and transmit the images to a television monitor (not illustrated) which is connected to the laparoscope camera and on which the images of the surgical field are displayed. Accordingly, the television monitor enables a surgical team to view the anatomical structure or structures in the surgical field inside the patient as the surgical procedure is carried out using laparoscopic surgical instruments.

Figure 8:
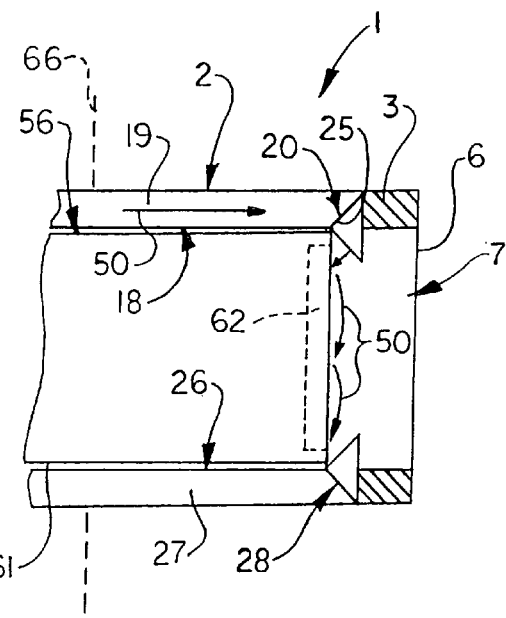
FIG. 8 is an enlarged longitudinal sectional view, partially in section, taken along section lines 3-3 in FIG. 2, of the cleaner sheath element of the laparoscopic lens cleaner, with the laparoscopic lens cleaner fitted on a laparoscope and more particularly illustrating typical discharging of a cleaning fluid from the laparoscopic lens cleaner and against the lens of the laparoscope.
Figure 9:
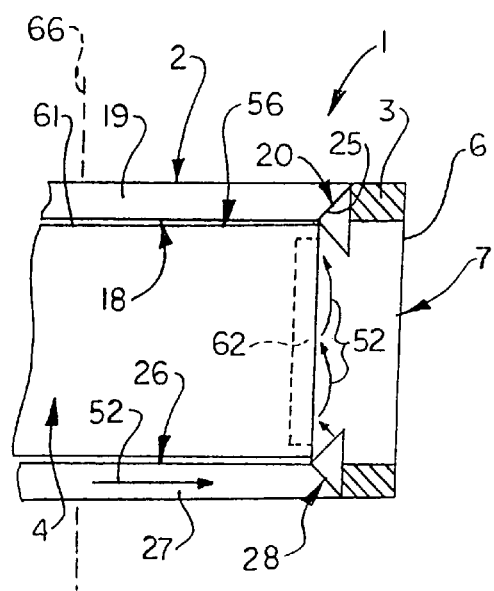
FIG. 9 is an enlarged longitudinal sectional view, partially in section, taken along section lines 3-3 in FIG. 2, of the cleaner sheath element of the laparoscopic lens cleaner, with the laparoscopic lens cleaner fitted on a laparoscope and more particularly illustrating typical discharging of a drying gas from the laparoscopic lens cleaner and against the lens of the laparoscope.
Figure 13:
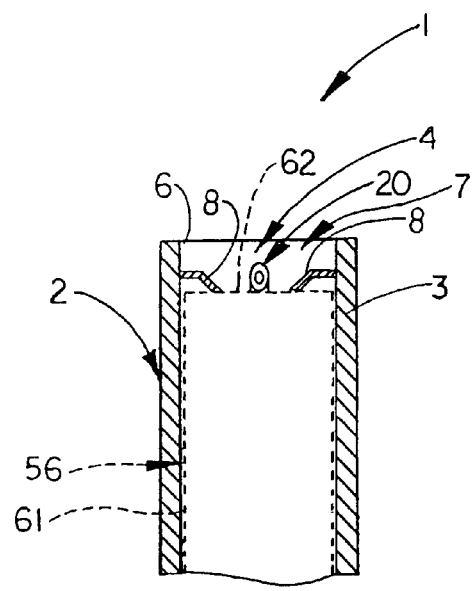
FIG. 13 is a longitudinal sectional view, partially in section, taken along section lines 13-13 in FIG. 2, more particularly illustrating a pair of spaced-apart sheath flanges provided in the cleaner sheath element of the laparoscopic lens cleaner and a laparoscope (in phantom) inserted in the cleaner sheath and engaging the sheath flanges.

Prior to the laparoscopic surgical procedure, the laparoscopic lens cleaner 1 is positioned on the lens shaft 61 of the laparoscope 56. This is accomplished typically by extending the lens shaft 61 of the laparoscope 56 through the sheath interior 4 of the cleaner sheath 2, as illustrated in FIG. 5, until the ring gasket 10 of the cleaner sheath 2 sealingly engages the laparoscope housing 57, as illustrated in FIG. 6. The attachment clip 14 on the cleaner sheath 2 is typically caused to engage the laparoscope housing 57, such as by, for example, engaging a housing notch 58 on the laparoscope housing 57 in the locking configuration of the attachment clip 14, as illustrated in FIG. 6, to detachably fasten the cleaner sheath 2 to the laparoscope 56. As illustrated in FIG. 13, when the cleaner sheath 2 is positioned on the lens shalt 61, the distal end of the lens shaft 61 engages the sheath flange or flanges 8 in the sheath interior 4 of the cleaner sheath 2. Furthermore, as illustrated in FIGS. 8 and 9, the laparoscope lens 62 (shown in phantom) is located adjacent to and directly in the discharge flow path of the fluid discharge nozzle 20 of the fluid conduit 18 and of the gas discharge nozzle 28 of the gas conduit 26. As illustrated in FIG. 1, the fluid connecting conduit 32 and the gas connecting conduit 36 of the laparoscopic lens cleaner 1 are connected to the fluid pump and supply apparatus 40 and the gas pump and supply apparatus 46, respectively, typically through the respective conduit connectors 33 and 37.

Figure 7:
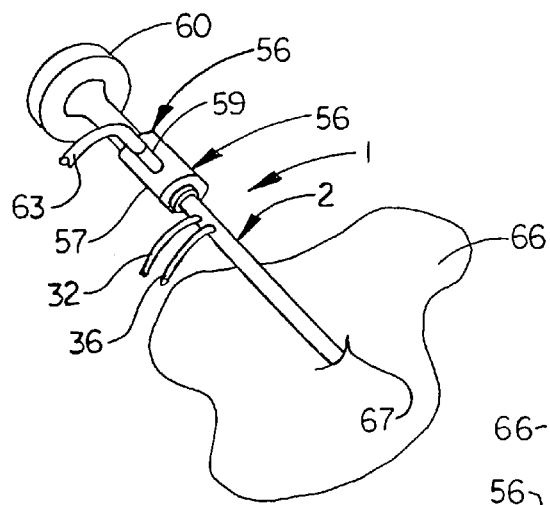
FIG. 7 is a perspective view of a laparoscope extending through an incision in a patient (partially in section), with the laparoscopic lens cleaner fitted on the laparoscope.

The laparoscopic surgical procedure is initiated by prepping the patient 66 typically in conventional fashion. As illustrated in FIG. 7, an incision 67 is cut typically through the abdominal wall of the patient 66. The cleaner sheath 2 of the laparoscopic lens cleaner 1, extending over the lens shaft 61 of the laparoscope 56, is inserted through the incision 67, with the laparoscope housing 57 of the laparoscope 56 remaining outside the patient 66. Inside the abdomen or pelvis of the patient 66, anatomical structures (not illustrated) which are to be viewed, repaired, removed or manipulated in the surgical field during the laparoscopic surgical procedure are typically initially sighted through the camera viewfinder 60 of the laparoscope 56. These images are also transmitted to the television monitor (not illustrated) by the laparoscopic camera (not illustrated), which is connected to the laparoscope housing 57 typically through the camera cord 63 and camera attachment nipple 59, and the images are displayed on the television monitor. Various laparoscopic surgical instruments (not illustrated) are extended into the patient 66 typically through cannula sleeves (not illustrated) which are inserted through the incision 67 and/or through a separate incision or incisions (not illustrated) which are cut through the abdominal wall of the patient 66. Therefore, the laparoscope 56 is used by the surgical team to view the surgical field, including the anatomical structure or structures typically in the abdominal or pelvic region of the patient 66, on the television monitor as the laparoscopic surgical instruments are manipulated to repair, remove or otherwise manipulate the structure or structures.

Throughout the laparoscopic surgical procedure, biological tissue or matter (not illustrated) has a tendency to enter the distal opening 7 of the cleaner sheath 2 of the laparoscopic lens cleaner 1 and contact the laparoscope lens 62 of the laparoscope 56. This tends to obscure the images of the surgical field as they are displayed on the television monitor. Therefore, the biological tissue or matter can be cleaned from the laparoscope lens 62 typically as follows. The fluid pump and supply apparatus 40 (FIG. 1) is initially operated to pump a cleaning fluid 50, such as saline solution, for example, through the fluid connecting conduit 32 and the fluid distribution segment 19 and fluid discharge nozzle 20, respectively, of the fluid conduit 18. As illustrated in FIG. 8, the cleaning fluid 50 is discharged from the fluid discharge nozzle 20 through the nozzle openings 22 (FIG. 11) in a spray pattern, or alternatively, through the single nozzle opening 23 (FIG. 12) in a single stream, against and across the surface of the laparoscopic lens 62. The cleaning fluid 50 dislodges the tissue or other matter (not illustrated) from the laparoscopic lens 62, substantially clearing the images of the surgical field which are displayed on the television monitor.

After the cleaning fluid 50 is discharged against the laparoscope lens 62, residual cleaning fluid 50 can be dried from the laparoscopic lens 62 as illustrated in FIG. 9, typically as follows. The gas pump and supply apparatus 46 (FIG. 1) is initially operated to pump a drying gas 52, such as carbon dioxide, for example, through the gas connecting conduit 36 and the gas distribution segment 27 and gas discharge nozzle 28, respectively, of the gas conduit 26. As illustrated in FIG. 9, the drying gas 52 is discharged from the gas discharge nozzle 28, against and across the surface of the laparoscopic lens 62. The drying gas 52 dries the residual cleaning fluid 50 from the laparoscopic lens 62 to prevent the residual cleaning fluid 52 from obscuring the images of the surgical field as they are displayed on the television monitor. The fluid pump and supply apparatus 40 and the gas pump and supply apparatus 46 can be operated as often as is necessary to rinse and dry, respectively, the laparoscope lens 62 of the laparoscope 56 and maintain clarity of the surgical field as it is displayed on the television monitor. It is understood that the apparatus can be disposable, as desired.

Referring next to FIGS. 14-18 of the drawings, an alternative illustrative embodiment of the laparoscopic lens cleaner is generally indicated by reference numeral 71. The laparoscopic lens cleaner 71 includes a generally elongated, cylindrical or tubular cleaner sheath 72 having a sheath wall 3 (FIG. 15) which may be a substantially rigid or semi-rigid plastic, for example. As illustrated in FIG. 15, the sheath wall 73 typically has a generally annular cross-sectional configuration and defines a sheath interior 74. As illustrated in FIG. 14, the cleaner sheath 72 has a proximal end 75 and a distal end 76 having a distal opening 77 (FIG. 16).

As illustrated in FIGS. 15, 16 and 18, at least two spacer studs 90, the purpose of which will be hereinafter described, may extend from the sheath wall 73 and into the sheath interior 74 in substantially diametrically-opposed relationship with respect to each other. As illustrated in FIG. 16, multiple spacer stud sets 91, each of which includes multiple spaced-apart spacer studs 90 distributed around the interior circumference of the sheath wall 73, may be disposed at spaced-apart intervals with respect to each other in the sheath interior 74 along the length of the cleaner sheath 72. As illustrated in FIG. 15, in some embodiments each spacer stud set 91 may include four spacer studs 90 which extend from the sheath wall 73 and into the sheath interior 74 in substantially equally spaced-apart relationship to each other. However, each spacer stud set 91 may include as few as two spacer studs 90 disposed in substantially diametrically-opposed relationship with respect to each other. Each spacer stud 90 may be a resilient material such as rubber or plastic, for example and without limitation.

A fluid conduit 78 is provided in the sheath interior 74 of the cleaner sheath 72 and includes an elongated fluid distribution segment 79 which extends generally parallel to the longitudinal axis of the cleaner sheath 72. As illustrated in FIG. 16, the fluid distribution segment 79 has an inlet end 84 which may be disposed at or adjacent to the proximal end 75 of the cleaner sheath 72 and an outlet end 85 which terminates at or adjacent to the distal end 76 of the cleaner sheath 72. As illustrated in FIGS. 15-18, the fluid distribution segment 79 of the fluid conduit 78 may extend within and along the sheath wall 73 of the cleaner sheath 72. The diameter or width of the fluid distribution segment 79 may be substantially equal to or slightly larger than the thickness of the sheath wall 73.

As illustrated in FIGS. 16 and 17, a fluid discharge nozzle 80, having at least one nozzle opening 82 (FIG. 17), communicates with the outlet end 85 of the fluid distribution segment 79 and protrudes into the sheath interior 74, typically adjacent to the distal end 76 of the cleaner sheath 72. The fluid discharge nozzle 80 may have a design which is similar to that of the fluid discharge nozzle 20 of the laparoscopic lens cleaner 1 heretofore described with respect to FIGS. 1-13. As illustrated in FIG. 14, a typically elongated, flexible fluid connecting conduit 32 is disposed in fluid communication with the inlet end 84 (FIG. 16) of the fluid distribution segment 79. The fluid connecting conduit 32 may extend from the cleaner sheath 72 through a fluid inlet opening 73a (FIG. 16) provided in the sheath wall 73. As further illustrated in FIG. 14, the fluid connecting conduit 32 is connected to the fluid reservoir 41 of the fluid pump and supply apparatus 40 such as through a suitable conduit connector 33, for example. As illustrated in FIGS. 16 and 17, a gas flow space 88 is defined by and between the exterior surface of the fluid conduit 78 and the interior surface of the sheath wall 73. Accordingly, the wall of the fluid distribution segment 79 of the fluid conduit 78 separates the gas flow space 88 from the interior of the fluid conduit 78.

As further illustrated in FIG. 14, a gas connecting conduit 36, which may be generally elongated and flexible, is disposed in fluid communication with the gas flow space 88 portion of the sheath interior 74. The gas connecting conduit 36 may extend through a gas inlet opening 73b (FIG. 16) which is provided in the sheath wall 73 of the cleaner sheath 72. As illustrated in FIG. 14, the gas connecting conduit 36 is connected to the gas reservoir 47 of the gas pump and supply apparatus 46.

Referring again to FIGS. 14, 17 and 18 of the drawings, in typical use, the laparoscopic lens cleaner 71 is extended over the laparoscope 56 (illustrated in phantom in FIGS. 17 and 18) to periodically clean and dry the laparoscope lens 62 of the laparoscope 56 during a laparoscopic surgical procedure. The laparoscope 56 may be similar in design to that which was heretofore described with respect to FIGS. 5 and 6. Prior to a laparoscopic surgical procedure, the laparoscopic lens cleaner 71 is positioned on the lens shaft 61 of the laparoscope 56. This is accomplished typically by extending the lens shaft 61 of the laparoscope 56 through the gas flow space 88 in the sheath interior 74 of the cleaner sheath 72 as the spacer studs 90 of the cleaner sheath 2 sealingly engage the exterior surface of the laparoscope housing 57, as illustrated in FIG. 18. As illustrated in FIG. 17, when the cleaner sheath 72 is positioned on the lens shaft 61, the laparoscope lens 62 (shown in phantom) is located adjacent to and directly in the discharge flow path of the fluid discharge nozzle 80 of the fluid conduit 78. As illustrated in FIGS. 17 and 18, the spacer studs 90 maintain separation between the lens shaft 61 of the laparoscope 56 and the sheath wall 73 of the cleaner sheath 72, defining a gas flow annulus 86 within the gas flow space 88 between the interior surface of the sheath wall 73 of the cleaner sheath 72 and the exterior surface of the lens shaft 61. As illustrated in FIGS. 17 and 18, the gas flow annulus 86 may be at least partially interrupted by the fluid distribution segment 79 of the fluid conduit 78. The wall of the fluid distribution segment 79 separates the gas flow annulus 86 from the interior of the fluid conduit 78.

As illustrated in FIG. 14, the fluid connecting conduit 32 and the gas connecting conduit 36 of the laparoscopic lens cleaner 71 are connected to the fluid pump and supply apparatus 40 and the gas pump and supply apparatus 46, respectively, typically through the respective conduit connectors 33 and 37. Throughout the laparoscopic surgical procedure, which may be carried out as was heretofore described with respect to FIG. 7, biological tissue or matter (not illustrated) has a tendency to enter the distal opening 77 of the cleaner sheath 72 of the laparoscopic lens cleaner 71 and contact the laparoscope lens 62 of the laparoscope 56. Therefore, the biological tissue or matter can be cleaned from the laparoscope lens 62 typically by initially operating the fluid pump and supply apparatus 40 (FIG. 14) to pump a cleaning fluid 50, such as saline solution, for example, through the fluid connecting conduit 32 and the fluid distribution segment 79 and fluid discharge nozzle 80, respectively, of the fluid conduit 78. As illustrated in FIG. 17, the cleaning fluid 50 is discharged from the fluid discharge nozzle 80 through the nozzle openings 82 in a spray pattern, or alternatively, through the single nozzle opening 82 in a single stream, against and across the surface of the laparoscopic lens 62. The cleaning fluid 50 dislodges the tissue or other matter (not illustrated) from the laparoscopic lens 62, substantially clearing the images of the surgical field which are displayed on the television monitor (not illustrated) to which the laparoscope 56 is attached.

After the cleaning fluid 50 is discharged against the laparoscope lens 62, residual cleaning fluid 50 can be dried from the laparoscopic lens 62 as illustrated in FIGS. 17 and 18, typically as follows. The gas pump and supply apparatus 46 (FIG. 14) is initially operated to pump the drying gas 52, such as carbon dioxide, for example, through the gas connecting conduit 36 and into the gas flow annulus 86 in the gas flow space 88 of the cleaner sheath 72. As illustrated in FIGS. 17 and 18, the drying gas 52 flows along a cyclical or linear path in the gas flow annulus 86 from the gas connecting conduit 36 toward the laparoscopic lens 62 of the laparoscope 56. The drying gas 52 flows against and across the surface of the laparoscopic lens 62, drying the residual cleaning fluid 50 from the laparoscopic lens 62 to prevent the residual cleaning fluid 52 from obscuring the images of the surgical field as they are displayed on the television monitor. The fluid pump and supply apparatus 40 and the gas pump and supply apparatus 46 can be operated as often as is necessary to rinse and dry, respectively, the laparoscope lens 62 of the laparoscope 56 and maintain clarity of the surgical field as it is displayed on the television monitor. It is understood that the apparatus can be disposable, as desired.

Referring next to FIGS. 19 and 20 of the drawings, an alternative illustrative embodiment of the laparoscopic lens cleaner is generally indicated by reference numeral 71a. The laparoscopic lens cleaner 71a may have a design which is similar to that of the laparoscopic lens cleaner 71 which was heretofore described with respect to FIGS. 14-18, except spacer rings 92 replace the respective spacer stud sets 91 of spacer studs 90 in the gas flow space 88 of the cleaner sheath 72. Each spacer ring 92 may be a resilient material such as rubber or plastic, for example, and has an annular spacer ring body 93. A central ring opening 95 extends through the spacer ring body 93. Multiple gas openings 94 extend through the spacer ring body 93 of each spacer ring 92 in spaced-apart relationship with respect to each other around the central ring opening 95. As illustrated in FIG. 19, the longitudinal axis of each gas opening 94 may be disposed in generally parallel relationship with respect to the longitudinal axis of the cleaner sheath 72. Accordingly, in use of the laparoscopic lens cleaner 71a, the lens shaft 61 (illustrated in phantom) of the laparoscope 56 is extended through the ring opening 95 of each spacer ring 92, as illustrated in FIGS. 19 and 20. The spacer ring body 93 of each spacer ring 92 maintains the gas flow annulus 86 between the exterior surface of the lens shaft 61 of the laparoscope 56 and the interior surface of the sheath wall 73 of the cleaner sheath 72.

Figure 21:
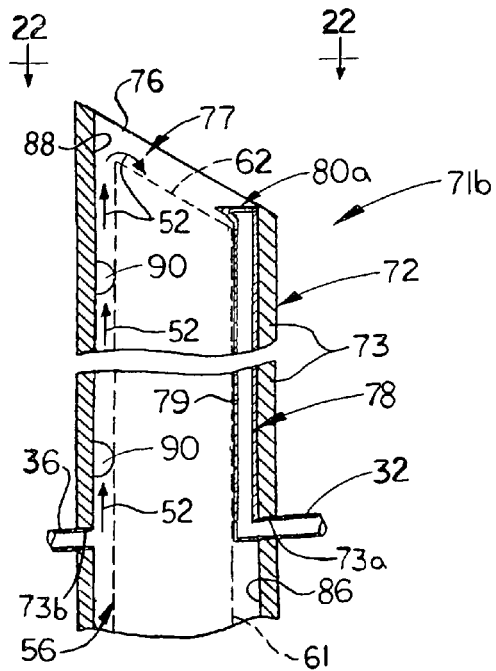
FIG. 21 is a longitudinal sectional view of a tapered cleaner sheath element of an alternative illustrative embodiment of the laparoscopic lens cleaner, with a tapered-profile laparoscope inserted in the cleaner sheath.
Figure 22:
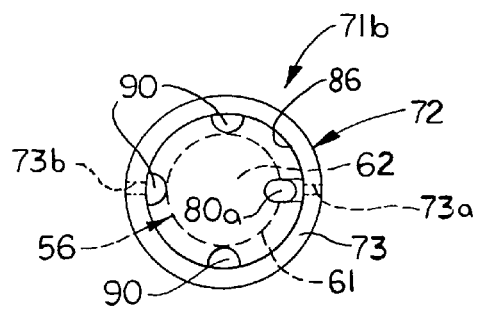
FIG. 22 is an end view, taken along viewing lines 22-22 in FIG. 21, of the tapered cleaner sheath of the laparoscopic lens cleaner.
Figure 23:
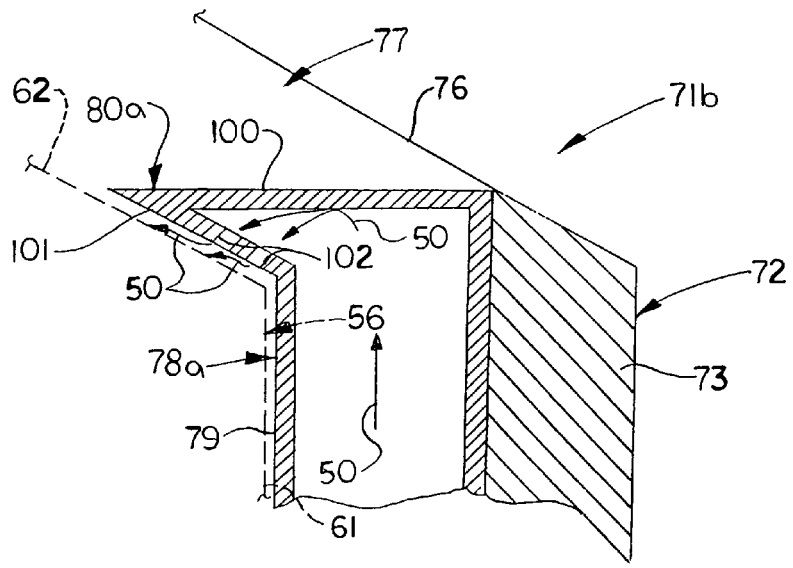
FIG. 23 is an enlarged sectional view, taken along section line 23 in FIG. 21, of a fluid discharge nozzle of a fluid conduit in the cleaner sheath.

Referring next to FIGS. 21-23 of the drawings, another alternative illustrative embodiment of the laparoscopic lens cleaner is generally indicated by reference numeral 71b. The laparoscopic lens cleaner 71b is adapted for use in conjunction with a laparoscope 56 having a tapered or angled laparoscope lens 62. Accordingly, as illustrated in FIG. 21, the sheath wall 73 of the cleaner sheath 72 may have a tapered or angled distal end 76 which may generally match the taper or angle of the laparoscope lens 62 of the laparoscope 56. A fluid conduit 78a is provided in the gas flow space 88. The fluid conduit 78a includes a generally elongated fluid distribution segment 79 which may be disposed along the interior surface of the sheath wall 73, as illustrated in FIG. 21. A fluid discharge nozzle 80a terminates the fluid distribution segment 79. As illustrated in FIG. 23, the fluid discharge nozzle 80a may include an end portion 100 which faces the tapered distal end 76 of the cleaner sheath 72 and a discharge portion 101 which is disposed at an acute angle with respect to the end portion 100. At least one fluid discharge opening 102 is provided in the discharge portion 101. When the laparoscope 56 is inserted in the gas flow space 88 in the sheath interior 74 of the cleaner sheath 72, the spacer studs 90 (FIG. 22) engage the lens shaft 61 of the laparoscope 56 and maintain the gas flow annulus 86 between the interior surface of the sheath wall 73 and the exterior surface of the lens shaft 61. Alternatively, the spacer rings 92 (FIGS. 19 and 20) may be provided in the sheath interior 74 in place of the spacer studs 90, in which case the lens shaft 61 extends through the ring opening 95 of each spacer ring 92. As illustrated in FIGS. 21 and 23, the fluid discharge opening or openings 102 in the fluid discharge nozzle 80a is/are directed toward the tapered or angled laparoscope lens 62 of the laparoscope 56. Accordingly, in operation of the laparoscopic lens cleaner 71b, as illustrated in FIG. 23, the cleaning fluid 50 is distributed through the fluid distribution segment 79 and then discharged through the fluid openings 102 of the fluid discharge nozzle 80a and against the laparoscopic lens 62 of the laparoscope 56, respectively. Drying gas 52 is distributed through the gas flow annulus 86 toward the distal end 76 of the cleaner sheath 72 and contacts and dries the laparoscope lens 62.

While the preferred embodiments have been described above, it will be recognized and understood that various modifications can be made and the appended claims are intended to cover all such modifications which may fall within the spirit and scope of the invention.

Having described my disclosure with the particularity set forth above, I claim:

1. A laparoscopic lens cleaner comprising:
   a generally elongated, tubular cleaner sheath having a sheath wall and a sheath interior defined by said sheath wall;
   a fluid conduit carried by said cleaner sheath;
   a fluid discharge nozzle communicating with said fluid conduit and extending into said sheath interior;
   a fluid connecting conduit communicating with said fluid conduit and extending from said cleaner sheath;
   a gas space occupying substantially a remaining volume in said sheath interior of said cleaner sheath and extending along respective sides of said fluid conduit;
   a gas connecting conduit communicating with said gas space and extending from said cleaner sheath; and
   a plurality of spacer studs provided in said sheath interior of said cleaner sheath.

2. The laparoscopic lens cleaner of claim 1 wherein sad cleaner sheath comprises a generally tubular sheath wall defining said sheath interior and wherein said fluid conduit extends within and along said sheath wall.

3. The laparoscopic lens cleaner of claim 1 wherein said plurality of spacer studs comprises four spacer studs carried by said cleaner sheath in equally spaced-apart relationship with respect to each other and extending into said sheath interior.

4. The laparoscopic lens cleaner of claim 1 further comprising a spring-biased attachment clip carried by said cleaner sheath.

5. The laparoscopic lens cleaner of claim 1 further comprising a ring gasket carried by said cleaner sheath.

* * * * *